United States Patent [19]

Gulliver et al.

[11] Patent Number: 5,019,777
[45] Date of Patent: May 28, 1991

[54] EDDY CURRENT TESTING PROGRAM WITH SCANNING PROBE HEAD HAVING PARALLEL AND NORMAL SENSING COILS

[75] Inventors: James A. Gulliver, Wantage; Christopher C. Holt, Abingdon; Kenneth D. Boness, Blewbury, all of England; Martin R. Anderson, deceased, late of Culham Station, England, by Donna J. Anderson, administratix

[73] Assignee: United Kingdom Atomic Energy Authority, London, England

[21] Appl. No.: 431,638

[22] Filed: Nov. 6, 1989

[30] Foreign Application Priority Data

Nov. 7, 1988 [GB] United Kingdom ............... 8825977

[51] Int. Cl.⁵ .................... G01N 27/90; G01R 33/12
[52] U.S. Cl. .................... 324/242; 324/202; 324/225; 324/227; 324/262
[58] Field of Search ............... 324/202, 217, 220, 225, 324/227, 239–243, 262

[56] References Cited

U.S. PATENT DOCUMENTS

| 2,889,514 | 6/1959 | Cowan et al. | 324/217 |
| 2,958,818 | 11/1960 | Cowan et al. | 324/217 |
| 3,504,276 | 3/1970 | Proctor et al. | 336/200 X |
| 3,875,502 | 4/1975 | Neumaier | 324/242 X |
| 4,325,026 | 4/1982 | Cooper, Jr. et al. | 324/219 X |

FOREIGN PATENT DOCUMENTS

| 0260355 | 3/1988 | European Pat. Off. | |
| 0739392 | 6/1980 | U.S.S.R. | 324/242 |
| 2201789 | 9/1988 | United Kingdom | |

Primary Examiner—Gerard R. Strecker
Attorney, Agent, or Firm—William R. Hinds

[57] ABSTRACT

An eddy current testing system consists of a multi-sensor probe, a computer and a special expansion card and software for data collection and analysis. The probe incorporates an excitation coil, and sensor coils; at least one sensor coil is a lateral current-normal coil and at least one is a current perturbation coil.

4 Claims, 3 Drawing Sheets

EDDY CURRENT TESTING PROGRAM WITH SCANNING PROBE HEAD HAVING PARALLEL AND NORMAL SENSING COILS

The detection of surface breaking defects in welds during subsea inspection of fixed steel structures is most commonly performed using close visual inspection or magnetic particle inspection techniques. Both of these methods usually require cleaning of the weldment surface to a high standard with substantial time and cost penalties, and they cannot easily be used to inspect coated structures.

Eddy current testing is potentially an ideal technique for rapid detection of surface breaking flaws, with a minimum of preparatory cleaning. Its use in this field has been limited both by experience of variable performance and the difficulties in applying existing eddy current instruments in the difficult subsea environment. These difficulties include the requirement to make multiple scans of a component, using complex scanning motions, and the difficulty of interpreting the vector plot data representations produced by standard instruments.

The present invention is designed to overcome the previous problems by a mixture of novel hardware and data display techniques. It enables an area of a component approximately 30 mm wide by typically 1 meter in length to be examined in a single pass, using a simple linear scanning motion. The data from the scan is displayed to the topside system operator and is easily interpreted by the operator. It is also possible to record the raw data from a scan on magnetic media for further analysis or component fingerprinting.

According to the present invention, there is provided an eddy current testing system including a multifaceted probe head for scanning in a predetermined direction and orientation over a surface of a body under test, the probe head having mounted thereon an exciting coil positioned with its axis parallel to the predetermined direction of scan for creating eddy currents in a body under test which circulate orthogonally to the direction of scan of the probe head, the exciting coil encompassing at least one eddy current sensing coil (hereafter sometimes referred to as a current-normal coil) having its coil axis parallel with the exciting coil axis and at least one eddy current sensing coil (hereafter sometimes referred to as a current perturbation coil) with its axis substantially normal to that of the exciting coil and adapted in use to be placed adjacent the surface of the body under test, means for producing driving signals and applying them to the exciting coil in the probe head, and means for processing and displaying signals produced in the sensing coils to indicate the presence of surface breaking discontinuities in the body under test.

A satisfactory eddy-current testing system should enable an operator to distinguish between cracks and material changes, such as changes in electrical resistivity or magnetic permeability, or changes in lift-off or orientation of the probe head. Distinguishing between cracks and increases in permeability is particularly difficult in high permeability material such as steel. By combining sensor coils of these two types, this has proved possible to achieve. The excitation coil is "lateral", i.e. its axis is parallel to the surface of an object under test, and its axis is parallel to the direction in which the probe head is scanned. The current-normal coil or coils are also "lateral", i.e. with their axes parallel to the surface, and also have their axes parallel to the direction in which the probe head is scanned; they are sensitive to any defect or crack along its whole length. The current perturbation coils are arranged with their axes substantially perpendicular to the axis of the driving coil; they are sensitive to the ends of any crack.

The eddy currents in a homogenous material approximate to a mirror image of the current in the excitation coil. Hence the excitation coil in this case creates eddy currents approximately normal to the expected crack direction. The current-normal coil or coils are desirably larger than the scale of localized variations in properties of the steel: this provides tolerance to lift-off, and reduces sensitivity to such variations. Preferably they are of diameter about 25 mm, desirably between about 10 mm and 50 mm, and may be polygonal or circular.

The invention will now be further described, by way of example only, and with reference to the accompanying drawings in which.

Figure 1:
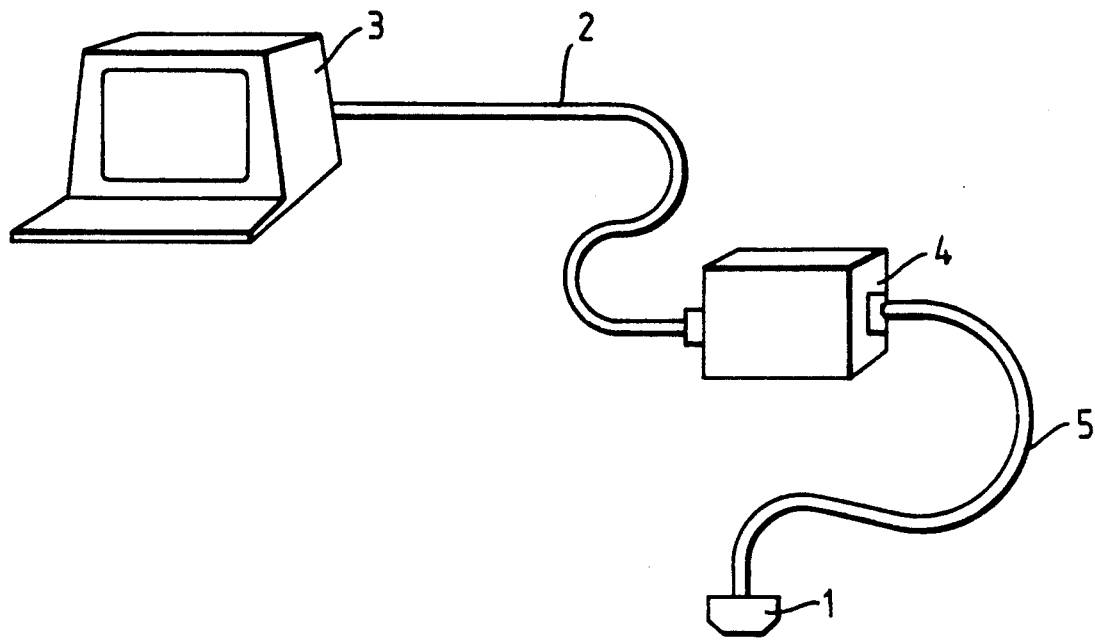
FIG. 1 is a general view of an instrument embodying the invention.

Referring to FIG. 1, the eddy current testing system of the present invention is based on a microcomputer 3. The main processing electronics for the system resides on a single full length expansion card in the computer enclosure. Signals are transmitted to and from a diver operated probe head 1 via an umbilical cable 2 connected at one end to an expansion card in the computer 3 and at the other end to a small electronics buffer/driver unit 4 adjacent to the test site. A further short length of umbilical cable 5 attaches the buffer/driver unit 4 to the probe head 1.

The Probe Head

The probe head 1 consists of a shaped moulding approximately 30 mm long by 40 mm wide. The shape of the head was determined by examination of the weld geometries which were to be met in the field trials of the instrument and takes into account most of the commonly encountered node geometries in off-shore steel structures. It is envisaged that a commercial version of the instrument will require a limited number of different probe heads to encompass the whole range of node geometries found in the offshore environment.

The probe head 1 includes a multiple array of sensor coils. The sensor coils are of two types, (a) one of which detects the presence or absence of a surface breaking defect along the whole of its length, and also detects the distance of the probe head 1 from the surface of the component, and (b) one which is sensitive to the ends of defects. The sensor coils are arranged in pairs to give the instruments ability to inspect an area of the component under test about 30 mm wide in a single pass.

Figure 2:
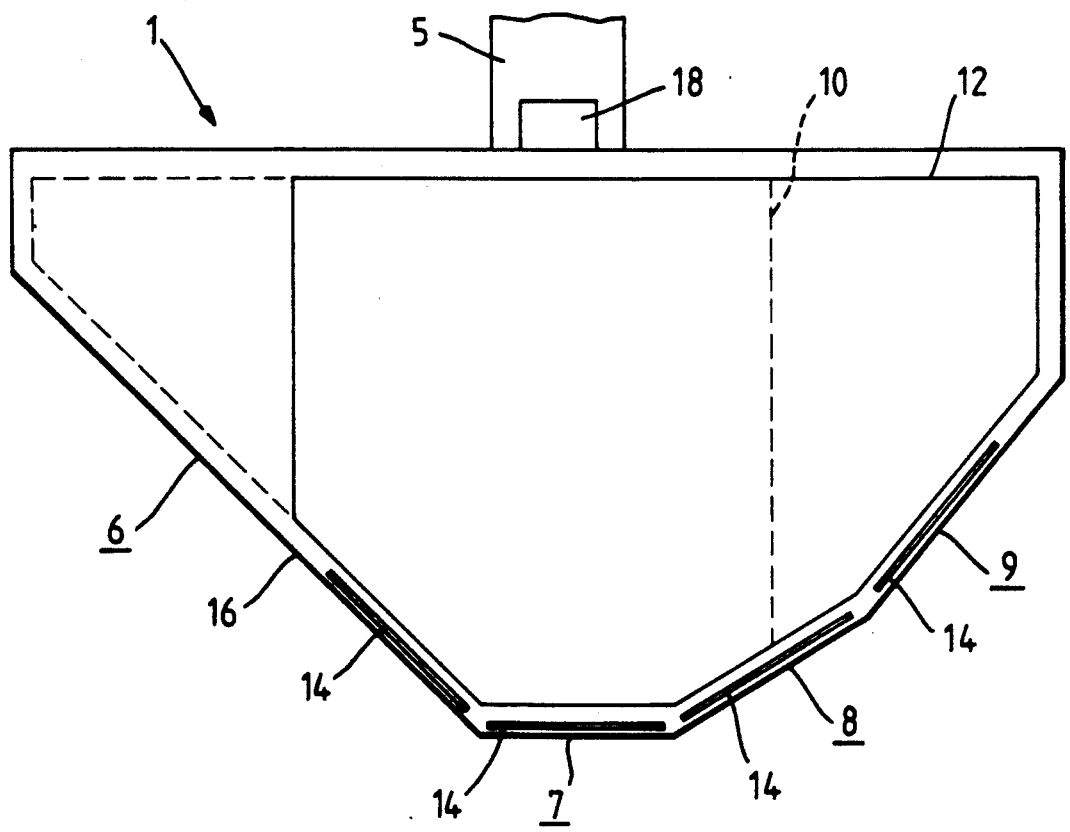
FIG. 2 is a diagrammatic end view of the probe head of the instrument of FIG. 1.

Referring now to FIG. 2 which is a diagrammatic end view showing the arrangement of the sensor coils in the probe head 1, the underside of the probe head 1 has four plane rectangular faces 6, 7, 8 and 9 at different inclinations: at angles of 30 degrees, 0 degrees, 22.5 degrees and 45 degrees to the horizontal, and the latter three are each 8 mm in width. This shape allows the probe to be fitted closely to the toes of most weld geometries. The optimum orientation of the probe during scanning is that which will maintain the largest area of contact of the lower faces of the probe to the component over the complete length of the scan path. This normally takes some experimentation by the diver, and judicious choice of the length of the scan to be undertaken.

The active sensor elements consist of two narrow, lateral, current-normal coils 10, 12 (one being indicated by a broken line), spaced apart along the length of the probe head 1, each of 60 polygonal turns of 0.125 mm diameter enamelled copper wire, and four flat current perturbation coils 14, each of 50 turns of 0.05 mm diameter enamelled copper wire. The two lateral current-normal coils 10 and 12 are staggered across the width of the probe head to provide a wide area of coverage of the component being examined. A current perturbation coil 14 is mounted onto each of the faces 6, 7, 8, 9 of the lower surface of the probe head 1 in small recesses in the coil winding former; each is wound on a long oval former about 4 mm wide and 16 mm long. The complete sensor coil assembly is potted in epoxy resin to hold the coils in place and to protect them from damage.

An excitation solenoid or coil 16 consisting of 50 turns of 0.3 mm diameter enamelled copper wire is wound over the sensor coil block, and the whole assembly is further potted in epoxy resin. The probe head 1 is completed by mounting a multiplexer and buffer amplifier assembly 18 on the top surface, connecting the sensor coils 10, 12, 14 to the multiplexer 18 and sealing and protecting these connections with a final layer of epoxy compound.

The lower end of the cable 5 and the top of the probe head 1 are further coated with a layer of flexible polyurethane potting compound to adhere to the cable sheath and to provide the necessary flexibility to alleviate the bending strains on the cable entry to the probe. Because the completed assembly is effectively a solid block, encapsulating the multiplexer 18 and the coils 10, 12, 14, 16, there is no path for water ingress, and the probe head 1 is suitable for work in the normal range of diving depths without any modification.

In use the probe head 1 is scanned by the diver, typically along a weld line as this is the most likely region for cracks to develop. The cracks are usually aligned approximately parallel to the weld line. The excitation coil 16 causes eddy currents normal to the weld line (or to a crack) and the current-normal coils 10, 12 are sensitive to such currents.

The Buffer/Driver Unit

The buffer/driver unit 4 is a small water-tight electronics box situated at the diver end of the main umbilical cable 2 and which connects to the probe head 1 via the short length of cable 5. This unit conditions the probe excitation signal transmitted down the main umbilical cable 2 from the processing electronics, and amplifies and buffers the sensor signals for transmission up the umbilical cable 2.

The cable 5 incorporates one coaxial cable carrying signals from the sensor coils 10, 12 or 14 via the multiplexer 18, three digital select lines carrying control signals to the multiplexer 18 to determine which sensor signal is to be transmitted, and a pair of twisted wires carrying current to the excitation coil 16. The buffer/driver unit 4 generates a current signal (of about 0.1 A) to supply to the excitation coil 16 in response to a voltage signal received from the computer 3 via the umbilical cable 2 (this signal is typically a continuous 40 kHz sine wave).

The Main Electronics Card

The main electronics card, residing in an expansion slot on the microcomputer 3 performs all of the hardware processing of the sensor signals, and generates the excitation waveform for the probe 1.

The card is programmable by the system software to process the incoming information with the optimum values of system parameters to maximise the signal to noise ratio and sensitivity of the processing. This allows the instrument to still be effective in detecting and locating defects over a wide range of probe lift off values.

With the current software and hardware configuration, the system is capable of interrogating all the sensor coils, and storing the data they produce, at rates of up to 100 scans per second. This represents a data resolution of 1 mm at a scanning rate of 100 mm per second. This speed is, in practice somewhat faster than is normally comfortable to a manual probe operator working on a welded node, so provision is made to select the rate of data acquisition from the computer keyboard.

System control and data analysis and presentation is effected by a 'user friendly' menu driven suite of software routines. The main menu allows details of the instrument settings, operator and component to be stored with the inspection data and gives access to the other system menus, which perform the business of the system. The main software functions are summarised below.

Calibration

Before commencing data acquisition on a component, and periodically during the work, it is necessary to calibrate the system, to ensure its performance is optimised to the prevailing conditions. The complete calibration process is very simple, and adds little to the time taken to perform an inspection.

The system is designed to operate with the sensor coils up to about 5 mm from the component surface. The software eliminates the effect of changing lift-off from the acquired data. This lift-off signal compensation is effective at lift-off values of ±2 mm from the calibration condition.

The calibration menu also allows the operator to view the derived system parameters and to perform a statistical analysis of the operation of the probe sensors. These facilities are useful to monitor the probe elements, and for system commissioning.

The first stage of signal processing is to null out any steady state signals from the selected sensor coil which do not carry any useful information about the component being tested. This process is necessary because the current-normal lateral coils 10, 12 present a large signal component which is transformer coupled into them directly from the excitation coil 16. The information-carrying part of the received signal is superimposed on this directly coupled signal, and is typically less than 10% of its amplitude. It is therefore desirable that the directly coupled signal component is removed from the input signal prior to further processing.

The offset compensation circuit subtracts from the input signals proportions of the master oscillator in-phase and quadrature outputs. The calculation of the correct proportions to be subtracted from the input signal is performed by a software algorithm during an offset calibration cycle. In this way a 'zero datum' for each sensor coil is established.

Following the offset compensation circuit is a programmable amplifier, which allows the overall gain of the processing electronics to be adjusted to maximise the use of the electronic dynamic range available in the system. Establishmint of the gain parameter for each sensor coil is carried out by the computer software during a gain calibration cycle. This ensures that the maximum signal which will be encountered during data acquisition lies just within the dynamic range of the system. For the current-normal coils 10, 12, this signal is represented by the received signal at infinite lift-off from the component being tested, so the gain calibration is performed with the probe head 1 removed from the component surface by at least 5 cm. Defect signals are typically 10%–20% of the amplitude of the lift off signal, and are 90 degrees out of phase with it. Thus, using the lift off signal amplitude to define the system gain allows the optimum setting of sensitivity to be made. The current perturbation coils 14 do not give rise to a lift off signal, so the gains for these channels are set to a preset value.

Therefore before scanning, the system is calibrated at the scanning position by placing the probe head 1 on the toe of the weld to be inspected, and the probe offset calibration performed. The probe is then removed from contact with the metal surface and the probe calibrated for lift off. This procedure normalises the gains for each of the sensor coils to give equal sensitivity and then nullifies the effect of lift off in the coils, as far as is possible.

Data Acquisition

The data acquisition menu enables the operator to set up scanning parameters and perform an inspection. Options are included to control the length of a scan, and the rate at which data is taken. Further options allow selection of data storage to a disc file for further analysis, identification of the component being tested, and whether to automatically analyse and display the results of the scan immediately after the scan is finished.

In operation, the data collection part of the software package regularly interrogates each of the sensor coils sequentially, and stores the two signal vector components (in phase and in quadrature) from each coil, after offset compensation and the appropriate gain, in a large memory array in digital form. After reading a sensor element, a delay of 1 ms is initiated by the hardware to allow the data from the next sensor to settle prior to its being digitised and read by the computer.

If the data storage option is enabled, the raw data from the component is stored on disc, along with all of the prevailing system parameters, and the scan position information. This allows a previously taken data set to be recalled at a later date, and analysed with all of the relevant parameters set to the same values as when the data was initially acquired.

Data Analysis and Display

This menu sets up the parameters for the analysis and display of the data taken during a scan, and also provides a route for recalling and displaying previously stored data files. By selection of the appropriate items from this menu, it is possible to display the data in either its analysed or its raw form. The analysis routines have been optimised during the laboratory development of the system to maximise detection reliability and ease of interpretation.

The data analysis routine performs matrix transformations of the data from each lateral coil 10, 12, to resolve the defect and lift off components of the signals, and smoothes the data to eliminate any high frequency noise in the data. Following this process, each of the differential channel signals (from the coils 14) is examined in turn, and excursions of these signals above a presettable threshold level are marked as possible defect extremities. The data are then displayed on the screen in a form pre-selected by the operator. Setting of the threshold level is not difficult in practice, and experience has shown that a novice operator of the system can correctly identify indications of defects within a short time of being introduced to the system.

Several data display options are available to the system operator. The most commonly used option presents the analysed results as shown in FIGS. 3 and 4.

Three lines of text at the top of the display give all of the relevant system parameters at the time of data collection. In the main body of the display, the following features appear. At the extreme left is a marker display, providing positional information. Such information may be provided orally by the diver to the top-side operator, indicating when the probe head 1 passes over pre-marked features or marks on the scan. To the right of this, the analysed sensor data are plotted, with the start of the scan at the top of the screen and the end of the scan at the bottom of the screen. Each trace represents the defect signal from one of the sensor coils 10, 12, 14 as it proceeds along the scan path.

In the examples shown, the traces may be thought of as four pairs of traces, with the left hand member of each pair being the signal from an absolute sensor coil (type (a) as defined earlier) i.e. one of the lateral coils 10 or 12, and the right hand member being the signal from the co-located transducer of type (b) which is sensitive to the ends of defects, i.e. the current perturbation coils 14.

Figure 3:
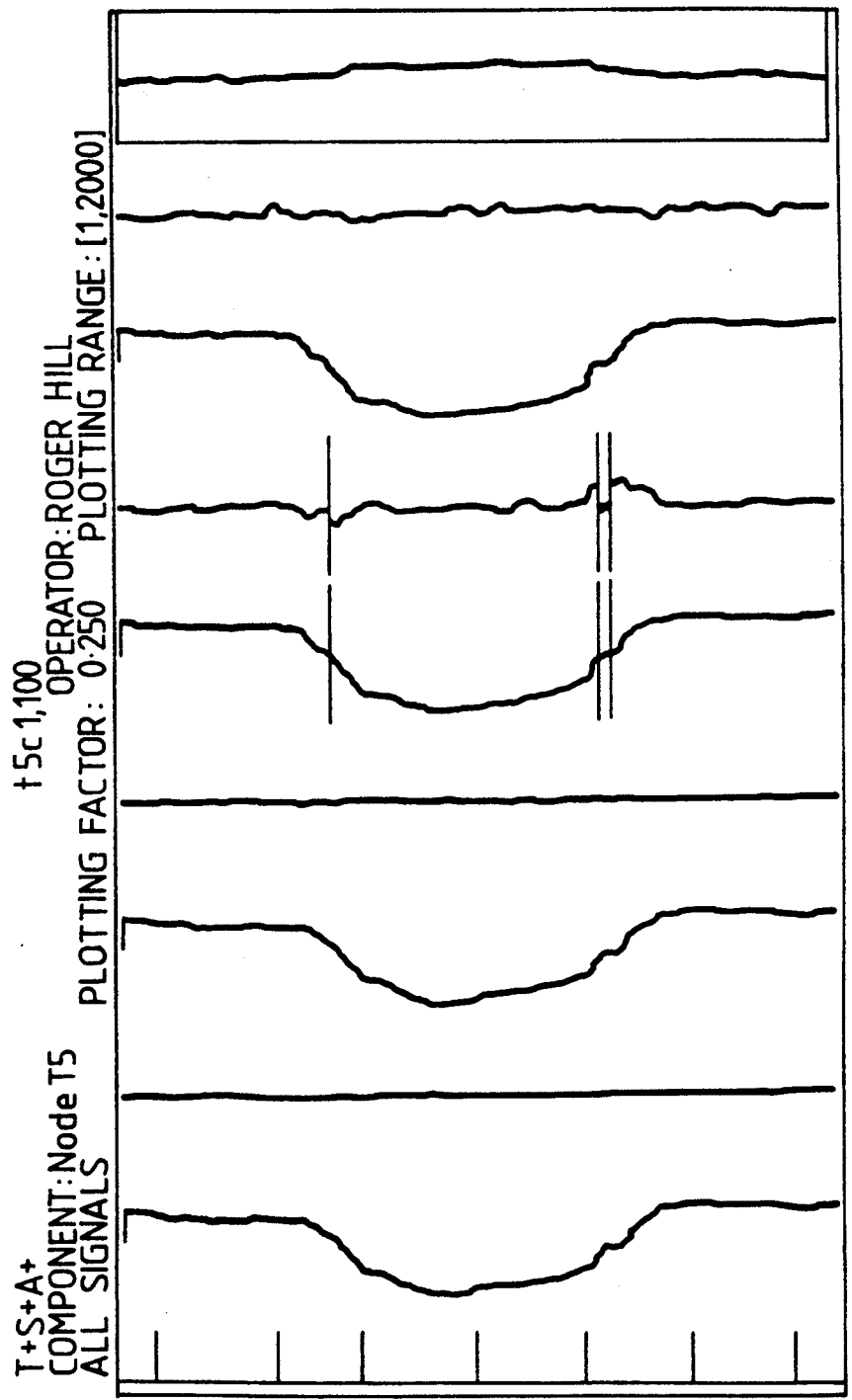
FIG. 3 is a representation of a data display indicating the presence of a fatigue crack in a weld.
Figure 4:
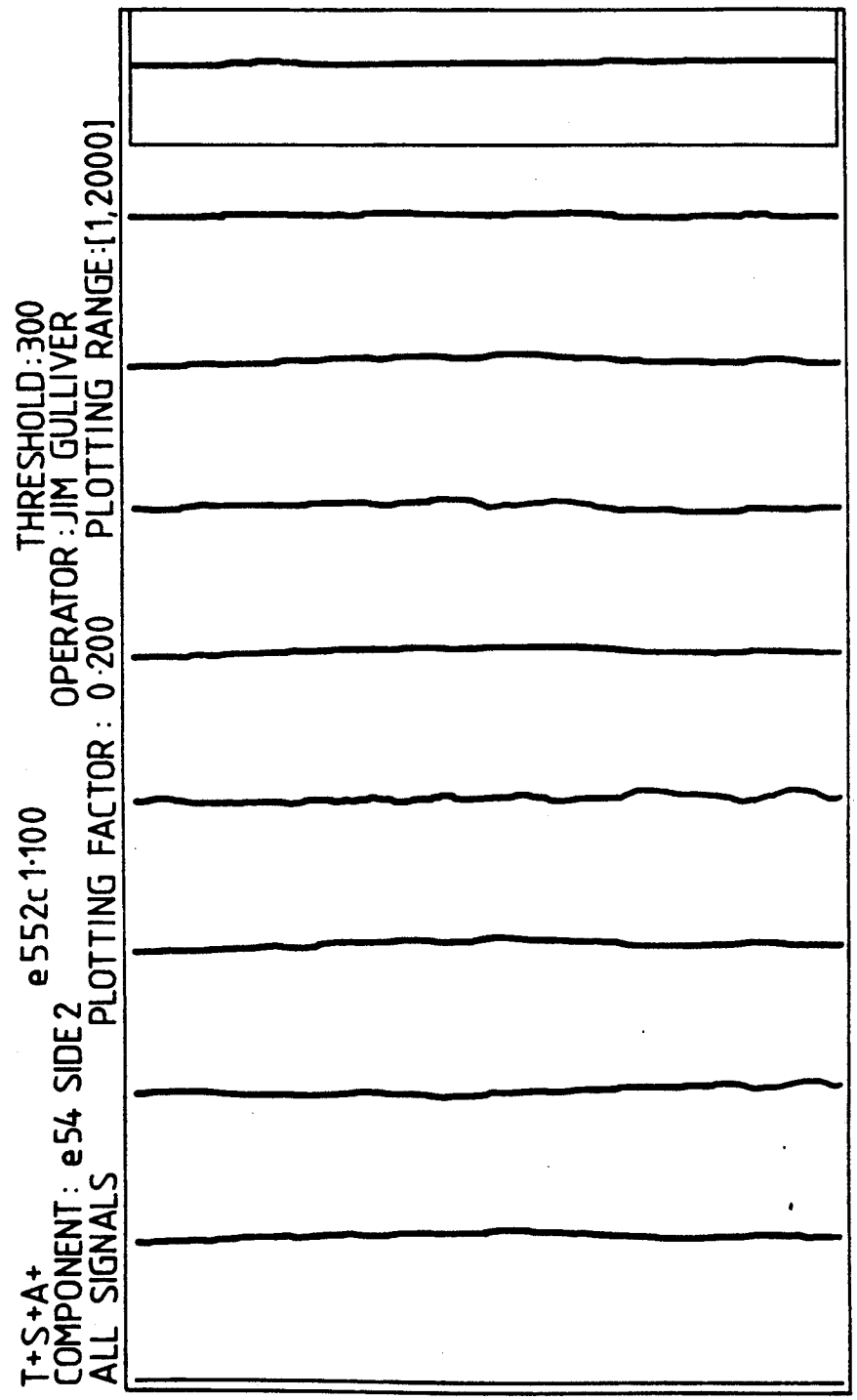
FIG. 4 is a representation of a data display showing a fault-free section of a weld.

FIG. 3 shows the response of each of these sensor types to a typical defect in the component under examination. The short horizontal bars on the display indicate where the type (b) sensor signal in that pair has exceeded the preset threshold, thus indicating the likely position of one extremity of a defect. The type (a) coils are less sensitive to probe location, and in this case the defect is visible in several channels. On the extreme right of the display, in a box of its own, an indication of probe lift-off is used to assess the quality of the scans.

FIG. 4 shows a scan over an uncracked region of a node weld.

The operator can select different portions of the display for more detailed inspection, and can change the scale on which each trace is displaced to further assist in the interpretation of the data.

This format of data presentation, together with the combination of sensor types, has proved to be a powerful aid for data interpretation and to be simpler and faster to apply than conventional impedance plane displays.

It will be appreciated that the probe head 1 might have a different shape to that described, and might incorporate a different number of sensor coils. For example if a wider area is to be scanned at once, a wider probe incorporating several lateral coils staggered across its width might be used. Each lateral coil may be circular or polygonal, and desirably its height is no less than 10 mm and its width no more than 40 mm; the larger its area the less sensitive it is to short cracks, but the smaller its area the more sensitive it is to small-scale variations in material properties such as permeability, which are commonly encountered in the vicinity of a weld.

We claim:

1. An eddy current testing system including a multi-faceted probe head for scanning in a predetermined direction and orientation over a surface of a body under test, said probe head having mounted thereon an exciting coil positioned with its axis parallel to the predetermined direction of scan for creating eddy currents in a body under test which circulate orthogonally to the direction of scan of the probe head, the exciting coil encompassing at least one eddy current sensing coil having its coil axis parallel with the exciting coil axis and at least one eddy current sensing coil with its axis substantially normal to that of the exciting coil and adapted in use to be placed adjacent the surface of the body under test, means for producing driving signals and applying them to the exciting coil in the probe head, and means for processing and displaying signals produced in the sensing coils to indicate the presence of surface breaking discontinuities in the body under test.

2. A system as claimed in claim 1 wherein each first-mentioned sensing coil has a width between 10 mm and 50 mm, and a height between 10 mm and 50 mm.

3. A system as claimed in claim 2 wherein each first-mentioned sensing coil has a width between 20 mm and 40 mm and a height between 10 mm and 25 mm.

4. A system as claimed in claim 1 wherein the processing and displaying means is arranged to determine and display graphically the variations in defect signal sensed by a first-mentioned sensing coil with position along the length of a scan, and also the variations in signal sensed by an adjacent second-mentioned sensing coil with position along the same scan.

* * * * *